(12) United States Patent
Yamada et al.

(10) Patent No.: US 10,813,660 B2
(45) Date of Patent: Oct. 27, 2020

(54) ULTRASONIC TREATMENT DEVICE

(71) Applicant: Olympus Corporation, Tokyo (JP)

(72) Inventors: Masashi Yamada, Sagamihara (JP);
Hideo Sanai, Hachioji (JP); Masami Oshida, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 553 days.

(21) Appl. No.: 15/260,362

(22) Filed: Sep. 9, 2016

(65) Prior Publication Data

US 2017/0007854 A1    Jan. 12, 2017

Related U.S. Application Data

(63) Continuation of application No. PCT/JP2016/063668, filed on May 6, 2016.

(30) Foreign Application Priority Data

Jun. 18, 2015  (JP) ................. 2015-122954

(51) Int. Cl.
*A61B 17/32*       (2006.01)
*A61B 17/00*       (2006.01)

(52) U.S. Cl.
CPC ............ *A61B 17/320068* (2013.01); *A61B 2017/0046* (2013.01); *A61B 2017/00477* (2013.01);
(Continued)

(58) Field of Classification Search
CPC ...... A61B 17/320068; A61B 17/22012; A61B 2017/320072; A61B 2017/0046; A61B 2017/00477
(Continued)

(56) References Cited

U.S. PATENT DOCUMENTS 6,051,010 A  *  4/2000  DiMatteo ......... A61B 17/22012
                                                606/169
6,068,647 A     5/2000  Witt et al.
(Continued)

FOREIGN PATENT DOCUMENTS

JP      2000-506431 A     5/2000
JP      2002-301086 A    10/2002
(Continued)

OTHER PUBLICATIONS

Japanese Office Action dated Feb. 7, 2017 received in Japanese Patent Application No. 2016-572337, together with an English-language translation.
(Continued)

*Primary Examiner* — Thomas A Giuliani
*Assistant Examiner* — Christine A Dedoulis
(74) *Attorney, Agent, or Firm* — Scully, Scott, Murphy & Presser, P.C.

(57) ABSTRACT

An ultrasonic treatment device includes a first vibration transmitting member and a second vibration transmitting member and being configured to treat a biological tissue by means of vibration transmitted by the first vibration transmitting member and the second vibration transmitting member. At a boundary position between the first vibration transmitting member and the second vibration transmitting member, the first vibration transmitting member has a boundary face including a contacting area that is in contact with the second vibration transmitting member at the face, and a non-contacting area that is not in contact with the second vibration transmitting member.

11 Claims, 9 Drawing Sheets

(52) U.S. Cl.
CPC .......... *A61B 2017/320071* (2017.08); *A61B 2017/320073* (2017.08); *A61B 2017/320082* (2017.08); *A61B 2017/320089* (2017.08)

(58) Field of Classification Search
USPC .......................................................... 606/27
See application file for complete search history.

(56) References Cited

U.S. PATENT DOCUMENTS

| 6,254,622 | B1* | 7/2001 | Hood | ............ | A61B 17/320068 |
|---|---|---|---|---|---|
| | | | | | 606/169 |
| 2002/0103438 | A1 | 8/2002 | Cronin et al. | | |
| 2007/0129723 | A1 | 6/2007 | Houser et al. | | |
| 2010/0298743 | A1* | 11/2010 | Nield | ............ | A61B 17/320068 |
| | | | | | 601/2 |
| 2015/0018726 | A1 | 1/2015 | Akagane | | |

FOREIGN PATENT DOCUMENTS

| JP | 2008-229357 | A | 10/2008 | | |
|---|---|---|---|---|---|
| JP | 2009-517181 | A | 4/2009 | | |
| JP | 2012-527325 | A | 11/2012 | | |
| WO | 98/27874 | A1 | 7/1998 | | |
| WO | 2014/065177 | A1 | 5/2014 | | |
| WO | WO-2014065177 | A1 * | 5/2014 | ............ | H04R 31/00 |

OTHER PUBLICATIONS

Japanese Final Office Action dated Jul. 11, 2017 received in Japanese Patent Application No. 2016-572337, together with an English-language translation.
International Search Report dated Aug. 2, 2016, received in International Application No. PCT/JP2016/063668.
International Preliminary Report on Patentability dated Dec. 28, 2017 received in International Application No. PCT/JP2016/063668.

* cited by examiner

ULTRASONIC TREATMENT DEVICE

TECHNICAL FIELD

The present invention relates to ultrasonic treatment devices.

BACKGROUND ART

A method to treat a biological tissue by means of ultrasonic vibration is available. While an ultrasonic transducer of the ultrasonic treatment device is used repeatedly, a distal-end part of the vibrating probe coming into contact with a biological tissue should be replaceable.

It is easier to replace the distal-end part of the probe in the configuration where the distal-end part of the probe is just pushed against to the proximal-end part than in the configuration where the distal-end part of the probe is fixed to the proximal-end part with a screw. When the distal-end part and the proximal-end part are in contact, having a spherical protrusion and a bowl-shaped recess, the contacting part has a linear shape, resulting in tendency to degrade the transmission efficiency of the vibration. Further considering the transmission efficiency of the vibration, the vibration characteristics and the positional relationship with the contacting part have to be examined.

SUMMARY OF THE INVENTION

The present invention aims to provide an ultrasonic treatment device that can transmit ultrasonic vibration effectively.

According to one aspect of the present invention, an ultrasonic treatment device includes: a first vibration transmitting member configured to transmit vibration along a reference line; and a second vibration transmitting member connected to the first vibration transmitting member in a non-screw manner, the second vibration transmitting member being configured to transmit vibration along the reference line together with the first vibration transmitting member, the ultrasonic treatment device being configured to treat a biological tissue by means of vibration transmitted by the first vibration transmitting member and the second vibration transmitting member, wherein at a boundary position between the first vibration transmitting member and the second vibration transmitting member, the first vibration transmitting member has a boundary face including a first contacting area that is in contact with the second vibration transmitting member at the face, and a first non-contacting area that is not in contact with the second vibration transmitting member.

The present invention can provide an ultrasonic treatment device that can transmit ultrasonic vibration effectively.

MODE FOR CARRYING OUT THE INVENTION

Main Embodiment

Figure 1:
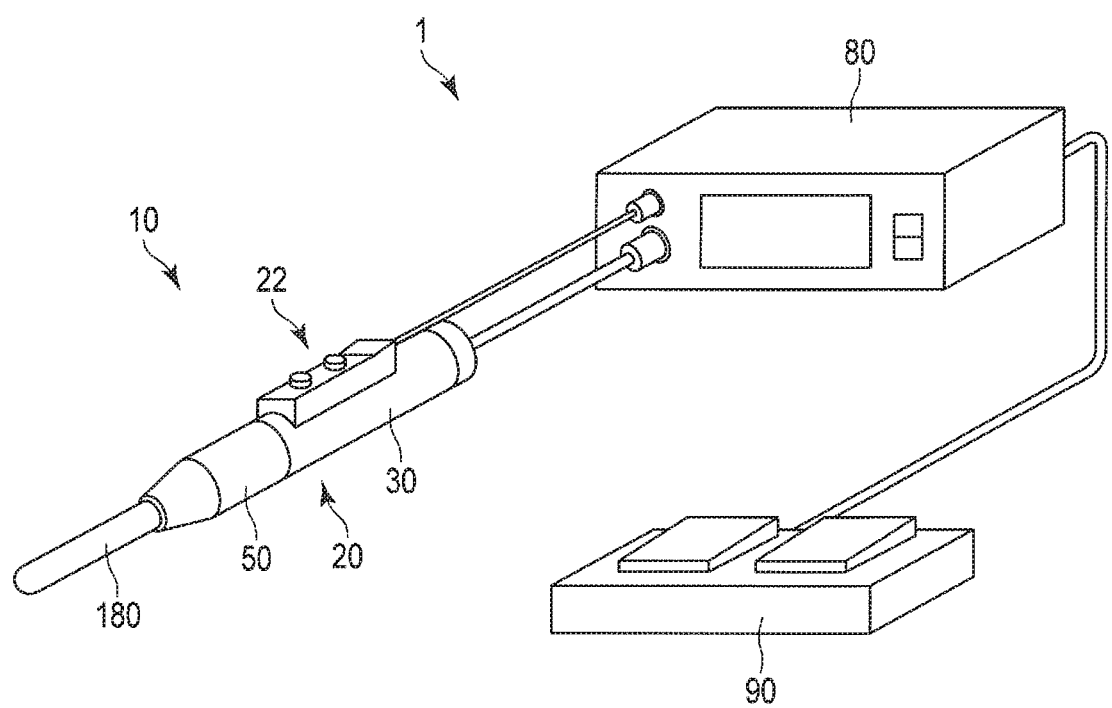
FIG. 1 schematically shows one example of the configuration of an ultrasonic treatment system according to one embodiment.

The following describes one embodiment of the present invention, with reference to the drawings. FIG. 1 schematically shows one example of the configuration of an ultrasonic treatment system 1 according to the present embodiment. As shown in this drawing, the ultrasonic treatment system 1 includes a treatment instrument 10 for a treatment with ultrasonic waves, a power supply 80 to supply electricity to the treatment instrument 10, and a foot switch 90.

The treatment instrument 10 includes a handpiece 20, and a distal-end probe 180 protruding from the handpiece 20. The handpiece 20 internally stores an ultrasonic transducer described later. Vibration generated at the ultrasonic transducer is transmitted to the distal-end probe 180 via an ultrasonic transmitting member disposed in the handpiece 20. As a result, the distal-end probe 180 vibrates ultrasonically. In the following description, one side close to the distal-end probe 180 is called a distal-end side, and the other side close to the handpiece 20 is called a proximal-end side.

The handpiece 20 is provided with an input 22. The input 22 receives instruction to drive the ultrasonic transducer. The input 22 may include a plurality of switches so as to enable a plurality of types of inputting corresponding to a plurality of types of driving of the ultrasonic transducer. The input part 22 is connected to the power supply 80. The ultrasonic transducer in the handpiece also is connected to the power supply 80. The power supply 80 detects the input to the input part 22, and supplies electricity corresponding to that to the ultrasonic transducer.

The foot switch 90 has a function similar to that of the input part 22 of the handpiece 20. That is, the foot switch 90 is provided with a switch similarly to the input part 22. Although switch 90 is described as a "foot" switch, switch 90 can be operated with any suitable appendage, such as a hand. Similarly to the input 22, the foot switch 90 may include a plurality of switches. When the power supply 80 detects an input to the foot switch 90, the power supply supplies electricity corresponding to the input to the ultrasonic transducer.

For use of the ultrasonic treatment system 1, a user holds the handpiece 20, and brings the ultrasonically-vibrating distal-end probe 180 into contact with a target biological tissue. At this time, the user manipulates the input 22 and/or the foot switch 90 to vibrate the ultrasonic transducer. Vibration generated at the ultrasonic transducer is transmitted to the distal-end probe 180. When the vibrating distal-end probe 180 and the biological tissue come into contact, heat is generated from the friction. Treatment, such as an incision, is performed to the target biological tissue by this heat. Note here that the ultrasonic treatment system 1 may function as a radio-frequency treatment instrument including the distal-end probe 180 as an electrode, in addition to ultrasonic vibration. In this embodiment, the ultrasonic treatment system 1 treats a biological tissue with ultrasonic vibration and radio-frequency electricity.

A part including the distal-end probe 180 can be disposable for hygiene. On the contrary, since a part including the ultrasonic transducer can be expensive, it can be used repeatedly. Then, the handpiece 20 of the treatment instrument 10, according to the present embodiment, is configured so that a handpiece body 30 on the proximal-end side and a handpiece distal portion 50, which supports the distal-end probe 180, are detachable.

Figure 2:
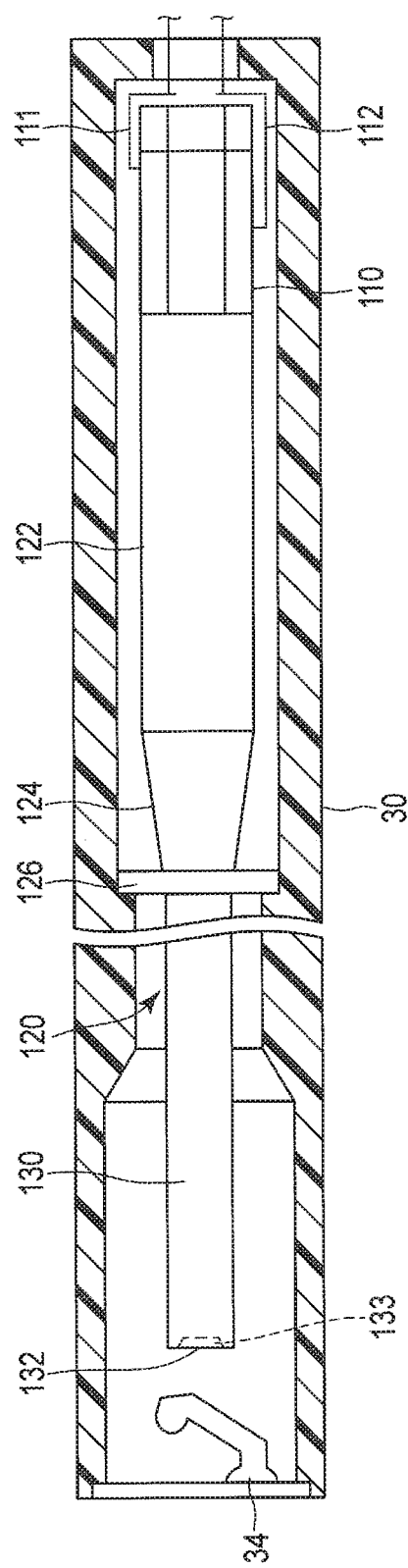
FIG. 2 schematically shows one example of the configuration of a handpiece body, an ultrasonic transducer, and an ultrasonic transmitting member.
Figure 3:
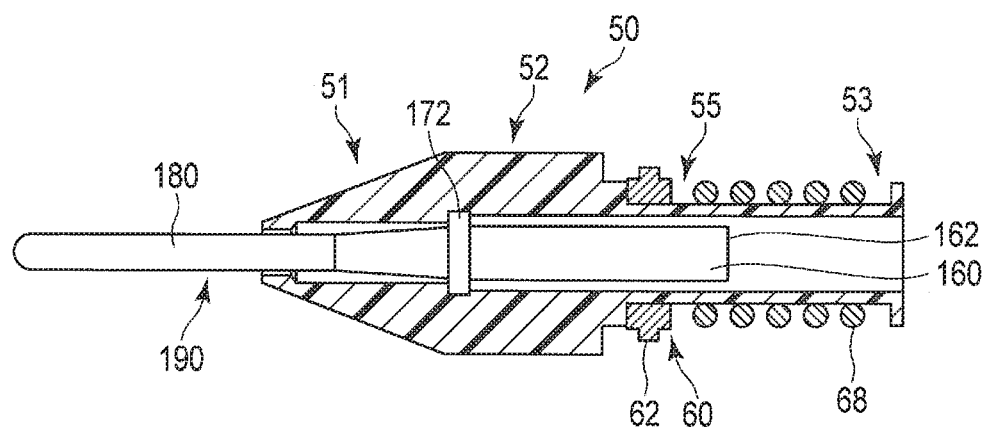
FIG. 3 schematically shows one example of the configuration of a handpiece distal portion and a probe member.
Figure 4:
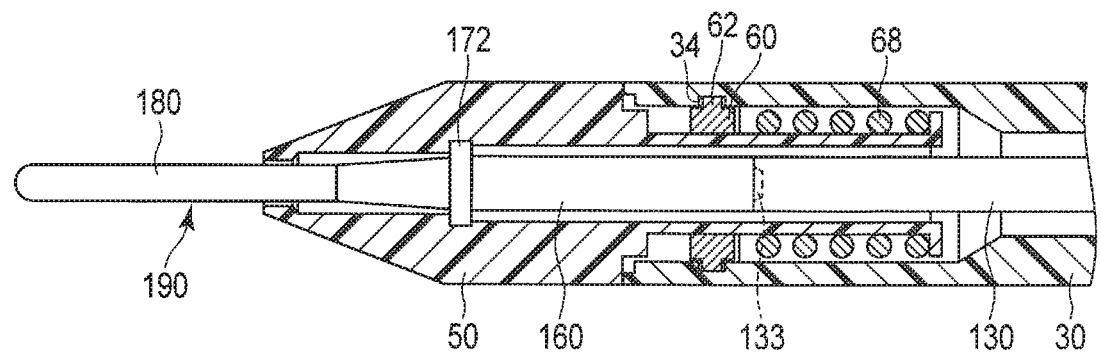
FIG. 4 shows one example of the state where a handpiece body and an ultrasonic transmitting member are attached to a handpiece distal portion and a probe member.

Referring now to FIGS. 2 to 4, connection between the handpiece body 30 and the handpiece distal portion 50 as well as connection between the ultrasonic transducer, the ultrasonic transmitting member and the distal-end probe 180 are described below.

FIG. 2 schematically illustrates one example of the configuration of the handpiece body 30 including an ultrasonic transducer 110. The handpiece body 30 roughly has a cylindrical shape, and has an internal space along a longitudinal axis configured to extend a distal portion of the handpiece body 30 to a proximal portion of the handpiece body 30 longitudinal axis. The handpiece body 30 can be made of a material with heat resistance as well as an electrical insulation property, such as plastic.

The ultrasonic transducer 110 can be disposed in the internal space of the handpiece body 30 on the proximal-end side. The ultrasonic transducer 110 can be a bolt-clamped Langevine type transducer (BLT), for example. Electricity is supplied from the power supply 80 to the ultrasonic transducer 110 via first wiring 111 and second wiring 112. The ultrasonic transducer 110 vibrates ultrasonically in accordance with this electricity. The ultrasonic transducer 110 is not limited to a BLT-type transducer, and various types of transducers can be used.

On the distal-end side of the ultrasonic transducer 110, an ultrasonic transmitting member 120 is disposed. The ultrasonic transmitting member 120 includes a transducer connecting portion 122, a horn 124, a flange 126, and a transducer-side transmitting portion 130 (first member). The ultrasonic transducer 110 on the distal-end side can be fixed to the transducer connecting portion 122 on the proximal-end side. On the distal-end side of the transducer connecting portion 122, the horn 124 is disposed, which is formed integrally with the transducer connecting portion 122. The horn 124 has a shape that becomes thinner from the proximal end to the distal end along the center axis. The horn 124 can increase the amplitude of ultrasonic vibration generated at the ultrasonic transducer 110. On the distal-end side of the horn 124, the flange 126 is disposed, which is formed integrally with the horn 124. On the distal-end side of the flange 126, the transducer-side transmitting portion 130 is disposed, which is formed integrally with the flange 126 and has a substantially cylindrical shape. In this embodiment, the transducer-side transmitting portion 130 has a diameter that is substantially the same along its longitudinal axis. Note here that, as described later in detail, the transducer-side transmitting portion 130 has a first surface 132 on the distal end, where a recess 133 is formed. The ultrasonic transmitting member 120 can be made of metal having favorable acoustic characteristics, such as, but not limited to, titanium alloy, stainless steel alloy, or aluminum alloy.

The flange 126 is fixed to the handpiece body 30. Herein the ultrasonic transducer 110 and the ultrasonic transmitting member 120 are not in contact with the inner wall of the handpiece body 30 at a part other than the flange 126. In this way, the ultrasonic transducer 110 and the ultrasonic transmitting member 120 are fixed within the internal space of the handpiece body 30. The transducer-side transmitting portion 130 of the ultrasonic transmitting member 120 is disposed in the internal space of the handpiece body 30 along the longitudinal axis, and the distal end of the transducer-side transmitting portion 130 is located close to the distal end of the handpiece body 30.

A groove 34 is formed on the inner face of the handpiece body 30 close to the distal end. The groove 34 is disposed so as to have an opening at the distal-end edge of the handpiece body 30. The groove 34 extends from the opening at the distal-end edge of the handpiece body 30 toward the proximal end of the handpiece body 30, and then is inclined in the circumferential direction while extending toward the proximal end of the handpiece body 30 and further extends in the circumferential direction so as to return toward the distal end of the handpiece body 30 at the most inward part. This groove has a width that is slightly larger than the outer diameter of a pin described later. The number of the groove 34 may be one groove or a plurality of grooves.

FIG. 3 schematically illustrates one example of the configuration of a part including the distal-end probe 180 and the handpiece distal portion 50. The handpiece distal portion 50 has a roughly cylindrical shape, and has an internal space along the center axis of the cylindrical shape. The handpiece distal portion 50 may be made up of a distal-end part 51, a center part 52, and a proximal-end part 53 along the longitudinal axis. At the center part 52, the handpiece distal portion 50 has an outer diameter that is substantially the same as the outer diameter of the handpiece body 30. At the distal-end part 51 that is closer to the distal end than the center part 52, the handpiece distal portion 50 has an outer diameter that becomes thinner toward the distal end. At the proximal-end part 53 that is closer to the proximal end than the center part 52, the handpiece distal portion 50 has an outer diameter that is smaller than the inner diameter of the handpiece body 30.

The proximal-end part 53 of the handpiece distal portion 50 has a depression 55 where the outer diameter is smaller than that of the proximal-end part 53. A slider ring 60 is fitted to this depression 55 so that its center axis coincides with the center axis of the handpiece distal portion 50. The slider ring 60 has an inner diameter that is slightly larger than the outer diameter of the depression. Therefore the slider ring 60 can move along the longitudinal axis in the depression 55. On the periphery of the slider ring 60, a pin 62 is disposed so as to correspond to the groove 34 of the handpiece body 30. That is, when two of the grooves 34 are disposed at intervals of 180° on the inner periphery of the handpiece body, for example, then two of the pins 62 are disposed at intervals of 180° on the outer periphery of the slider ring.

In the depression 55, a coil spring 68 is disposed so that its center axis coincides with the center axis of the handpiece distal portion 50. The coil spring 68 is disposed closer to the proximal end than the slider ring 60. The coil spring 68 is to apply a force to the slider ring 60 so as to push the slider ring 60 toward the distal end. Alternatively the coil spring 68 is to apply a force to a face of the depression 55 on the proximal-end side so as to push the handpiece distal portion 50 toward the proximal end.

Inside of the handpiece distal portion 50, a probe member 190 including the distal-end probe 180 is disposed. The probe member 190 is made of metal having favorable acoustic characteristics, such as, for instance, titanium alloy, stainless steel alloy, or aluminum alloy. The probe member 190 is made up of the distal-end probe 180, a flange 172 and a probe-side transmitting portion 160 (second member) arranged in this order from the distal-end side. That is, on the proximal-end side of the distal-end probe 180, the flange 172 is disposed. On the proximal-end side of the flange 172, the probe-side transmitting portion 160 is disposed.

In the present embodiment, the probe-side transmitting portion 160 has an outer diameter that is substantially equal to the outer diameter of the transducer-side transmitting portion 130. The distal-end probe 180 has an outer diameter that is the outer diameter or less of the probe-side transmitting portion 160. Therefore, when the distal-end probe 180 and the probe-side transmitting portion 160 have different outer diameters, the probe member 190 becomes thinner at a part provided with the flange 172 from the proximal end to the distal end.

The flange 172 of the probe member 190 is fixed to the handpiece distal portion 50. The probe member 190 is not in contact with the inner wall of the handpiece distal portion 50 at a part other than the flange 172. In this way, the probe member 190 is supported in the internal space of the handpiece distal portion 50 so that its longitudinal axis substantially coincides with the longitudinal axis of the handpiece distal portion 50. The probe-side transmitting portion 160 has a first surface 162 on the proximal-end side that is located at a part of the handpiece distal portion 50 close to the proximal end.

FIG. 4 schematically illustrates the state where the handpiece distal portion 50 is attached to the handpiece body 30. As shown in FIG. 4, the pin 62 of the slider ring 60 is inserted into the most inward part of the groove 34 formed on the inner face of the handpiece body 30 at a part close to the distal end. Since a force toward the distal end is applied to the slider ring 60 the pin 62 is latched at the most inward part of the groove 34 due to the elastic force of the coil spring 68. At this time, the inner wall of the handpiece body 30 on the distal end side is opposed to the outer wall of the proximal-end part 53 of the handpiece distal portion 50 close to the distal end. Then the distal-end face of the handpiece body 30 is opposed to the proximal-end face of the center part 52 of the hand piece distal portion 50.

Since the slider ring 60 is fixed to the handpiece body 30, the elastic force of the coil spring 68 acts so as to push the proximal-end face of the depression 55 of the handpiece distal portion 50 toward the proximal end. Therefore the handpiece distal portion 50 as a whole is pushed toward the proximal end.

Figure 5:
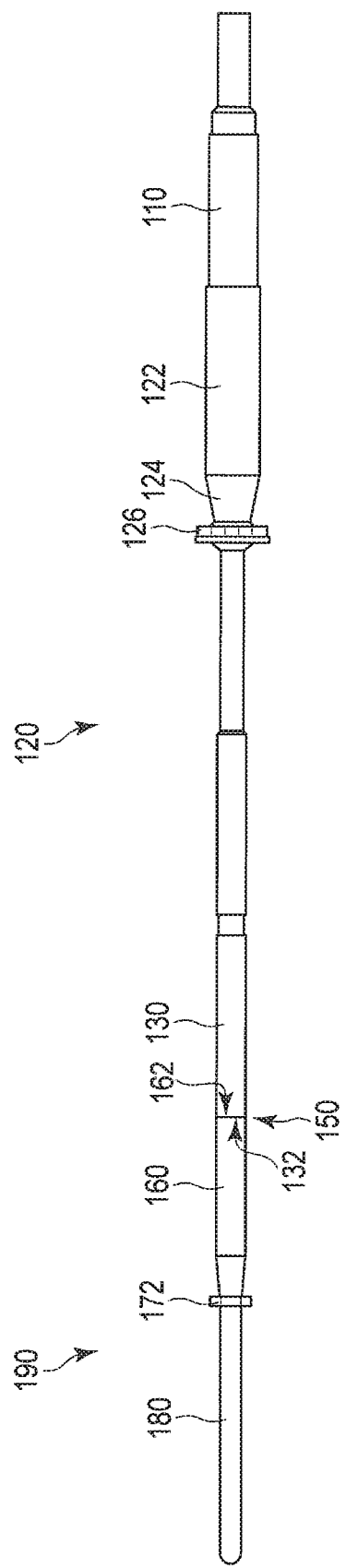
FIG. 5 schematically shows one example of the configuration of an ultrasonic transducer, an ultrasonic transmitting member and a probe member that are connected.

Since the probe member 190 is fixed to the handpiece distal portion 50, the probe member 190 is pushed toward the proximal end with reference to the ultrasonic transmitting member 120. As illustrated in FIG. 5, the ultrasonic transmitting member 120 and the probe member 190 are disposed so that the first surface 132 of the ultrasonic transmitting member 120 on the distal-end side and the first surface 162 of the probe member 190 on the proximal-end side are pushed against each other. In this configuration, vibration generated at the ultrasonic transducer 110 is transmitted to the probe member 190 via the ultrasonic transmitting member 120.

FIG. 5 schematically illustrates the connection of the ultrasonic transducer 110, the ultrasonic transmitting member 120 and the probe member 190. As described above, the ultrasonic transducer 110 and the ultrasonic transmitting member 120 are fixed to the handpiece body 30 at the flange 126. The probe member 190 is fixed to the handpiece distal portion 50 at the flange 172. The probe member 190 receives, at the flange 172, an external force toward the proximal end from the handpiece distal portion 50. This external force allows a connection between the ultrasonic transmitting member 120 and the probe member 190 at a connection position 150 by being pushed against each other (press-fit). In this way, the ultrasonic transducer 110, the ultrasonic transmitting member 120 and the probe member 190 are connected.

Ultrasonic vibration generated at the ultrasonic transducer 110 is transmitted to the probe member 190 via the ultrasonic transmitting member 120. As a result, the distal-end probe 180 vibrates. In this way, the combination of the ultrasonic transducer 110, the ultrasonic transmitting member 120 and the probe member 190 constitutes one vibration system. Herein, this vibration system is configured as follows. This configuration aids in substantially maintaining the relative positions of the components during operation.

The positions of the flange 126 of the ultrasonic transmitting member 120 and of the flange 172 of the probe member 190 are designed so as to coincide with node positions of the vibration. This is because substantial displacement does not occur in a vibrating body at the node positions of the vibration. Since displacement substantially does not occur in the vibrating body at the node positions, a contact with the handpiece body 30 or the handpiece distal portion 50 at these positions does not disturb the vibration due to the handpiece body 30 or the handpiece distal portion 50.

The connection position 150 at the boundary between the ultrasonic transmitting member 120 and the probe member 190 is designed so as to coincide with an antinode position of the vibration. This is because, at antinode positions of the vibration, while large displacement occurs at the vibrating body, local deformation of the vibrating body is small because stress applied to the vibrating body is small. Due to the location of the connection position 150, a contacting state of the ultrasonic transmitting member 120 and the probe member 190 is substantially unchanged. Such disposition of the connection position 150 at an antinode position of the vibration allows vibration to be transmitted from the ultrasonic transmitting member 120 to the probe member 190.

Figure 6:
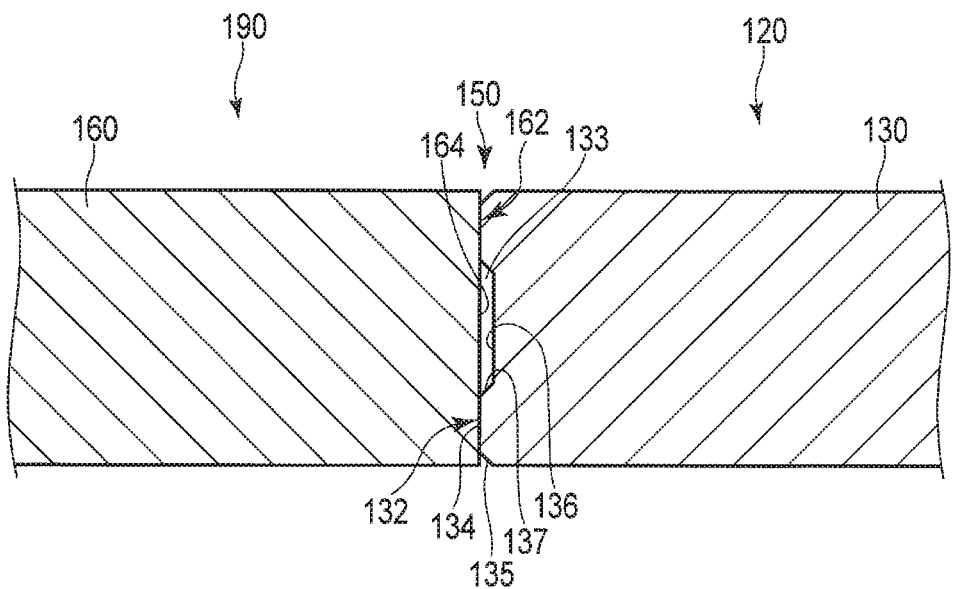
FIG. 6 shows one example of a connection position when the transducer-side transmitting portion of the ultrasonic transmitting member and the probe-side transmitting portion of the probe member are connected.

Referring next to FIG. 6, the details of the connection position 150 between the probe member 190 and the ultrasonic transmitting member 120 are described. The probe-side transmitting portion 160 of the probe member 190 has a cylindrical shape. The first surface 162 of the probe-side transmitting portion 160 on the proximal-end side is substantially flat. The transducer-side transmitting portion 130 of the ultrasonic transmitting member 120 also has a cylindrical shape. A recess 133 is formed at a substantially center part of the first surface 132 that is the face of the transducer-side transmitting portion 130 on the distal-end side. A face 164 is a part of the first surface 162 of the probe-side transmitting portion 160A. A bottom part 136 is a part of the first surface 132 of the transducer-side transmitting portion 130. The face 164 is configured to face the bottom part 136.

Figure 7:
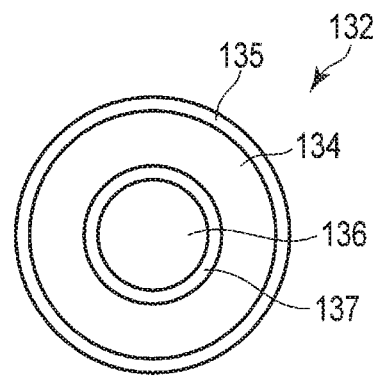
FIG. 7 shows one example of a first surface of the transducer-side transmitting portion on the distal-end side.

FIG. 7 illustrates the configuration of the first surface 132 as the boundary face that is viewed from the distal end. As shown in FIG. 7, the first surface 132 has an annular contact face 134 that comes into contact with the first surface 162. The recess 133 is formed on the bottom part 136. The bottom part 136 is configured to form a circular shape. The outer edge of the contact face 134 is chamfered, so that a chamfered part 135 is formed that is inclined with reference to the contact face 134. The contact face 134 has an inclined face 137 on the inner edge as well that is continuous with the bottom part 136. In this embodiment the bottom part 136 of the recess 133 is a circle, and the contact face 134 is annular as one example, but in other embodiments their shapes are not limited circular and can be any other suitable shape. For instance, the bottom part 136 of the recess 133 may be a rectangle, and the contact face 134 may be in a ring form that is angular at the four corners.

Due to such a recess 133 provided at the first surface 132, even when the actual resonant frequency of the vibration system is different from the theoretical value, the connection position 150 between the ultrasonic transmitting member 120 and the probe member 190 substantially corresponds to an antinode position of the vibration, and therefore the efficiency to transmit vibration from the ultrasonic transmitting member 120 to the probe member 190 is unlikely to substantially decrease.

Figure 8:
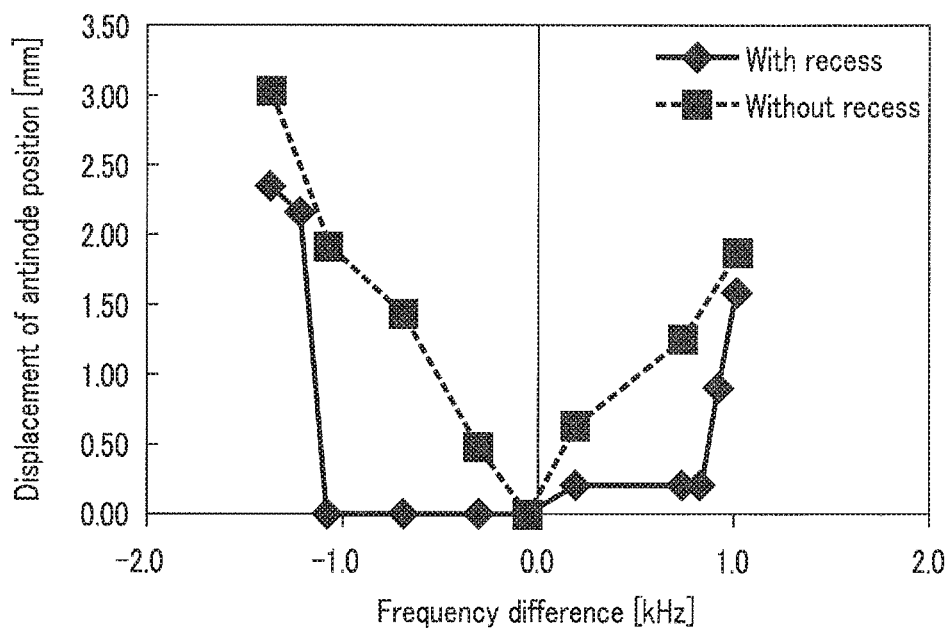
FIG. 8 shows one example of a numerical calculation of the displacement of antinode positions with reference to the frequency difference.

FIG. 8 shows one example of the simulation result of the relationship between displacement of antinode positions and a difference (called a frequency change) between a frequency change resulting from the ultrasonic transmitting member 120 and a frequency change resulting from the probe member 190. The simulation is based on the Pro/Mechanica. In FIG. 8, the solid line shows the relationship when the first surface 132 has the recess 133 as in the present embodiment, and the broken line shows the relationship in a comparative example, in which the first surface 132 does not have a recess 133, that is, the first surface 132 is flat. As illustrated in FIG. 8, when the frequency difference is 0, that is, when the frequency characteristics of the ultrasonic transmitting member 120 and the frequency characteristics of the probe member 190 are same as designed values, an antinode position will coincide with the boundary position between the ultrasonic transmitting member 120 and the probe member 190, regardless of whether the first surface 132 has the recess 133 or not. When the first surface 132 does not have a recess 133, as the frequency difference increases, the displacement of antinode positions accordingly increases. On the contrary, when the first surface 132 has the recess 133, the displacement of antinode positions occurs at a lesser amount, even with a frequency difference of about ±1 kHz.

The reason why the recess 133 at the first surface 132 can suppress the displacement of antinode positions is described below. As illustrated in FIG. 6, the first surface 132 is in contact with the first surface 162 at the contact face 134. The bottom part 136 corresponds to an antinode of the vibration. The face 164 of the first surface 162 facing the bottom part 136 corresponds to an antinode of the vibration. Since the bottom part 136 and the face 164 facing the bottom part 136 correspond to an antinode of the vibration, the connection position 150 including the contact face 134 also substantially corresponds to the antinode position. That is, even when the frequency characteristics of the ultrasonic transmitting member 120 and the probe member 190 change, the bottom part 136 and the face 164 facing the bottom part 136 are free ends and substantially correspond to an antinode of the vibration. As a result, even when the frequency characteristics of the ultrasonic transmitting member 120 and the probe member 190 change, the connection position 150 including the contact face 134 substantially corresponds to an antinode position.

The ultrasonic transmitting member 120 and the probe member 190 can be manufactured as designed. However, their vibration characteristics may change due to a manufacturing inaccuracy or the frequency of use or the elapsed time. The recess 133 is provided at the first surface 132 of the ultrasonic transmitting member 120 as in the present embodiment, whereby a change in antinode positions can be suppressed in spite of a manufacturing inaccuracy or aging, and as a result decrease in efficiency of vibration transmission can be reduced.

In this way, the transducer-side transmitting portion 130 is a first vibration transmitting member and the probe-side transmitting portion 160 is a second vibration transmitting member, then the first surface 132 corresponds to a boundary face of the first vibration transmitting member at the boundary position between the first vibration transmitting member and the second vibration transmitting member. That is, the first surface 132 is a boundary face that is visible when the first vibration transmitting member is viewed from the second vibration transmitting member along the center line as a reference line. Then the contact face 134 corresponds to a first contacting area that is in contact with the second vibration transmitting member, and the bottom part 136 corresponds to a first non-contacting area that is not in contact with the second vibration transmitting member.

When the probe-side transmitting portion 160 is a first vibration transmitting member and the transducer-side transmitting portion 130 is a second vibration transmitting member, the first surface 162 corresponds to a boundary face of the first vibration transmitting member at the boundary position between the first vibration transmitting member and the second vibration transmitting member. That is, the first surface 162 is a boundary face that is visible when the first vibration transmitting member is viewed from the second vibration transmitting member along the center line as a reference line. Then the face of the first surface 162 facing the contact face 134 corresponds to a first contacting area that is in contact with the second vibration transmitting member, and the face 164 facing the bottom part 136 corresponds to a first non-contacting area that is not in contact with the second vibration transmitting member.

MODIFICATION EXAMPLES

Some modification examples of the embodiment as stated above are described below. In the following, a difference from the embodiment as stated above is described, and the same reference numerals are assigned to the same parts to omit their descriptions.

First Modification Example

Figure 9:
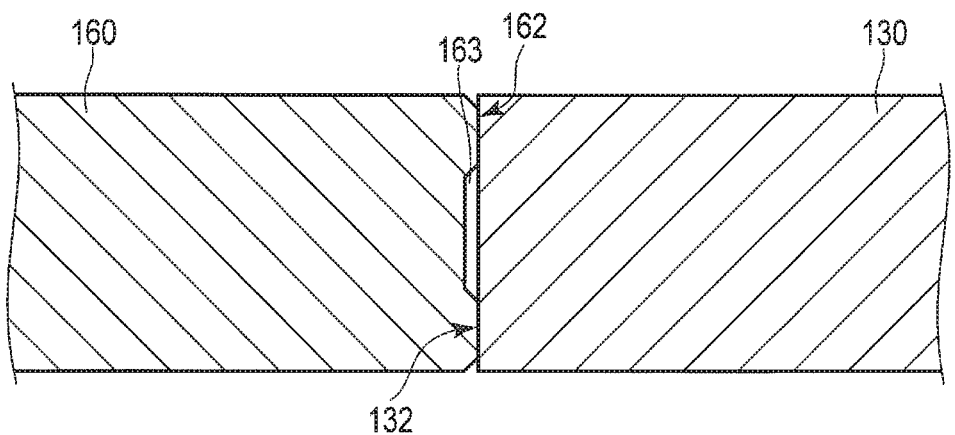
FIG. 9 shows one example of the configuration of the transducer-side transmitting portion and the probe-side transmitting portion in a first modification example.

Referring to FIG. 9, the configuration of a first modification example is described below. In the main embodiment, the first surface 132 of the transducer-side transmitting portion 130 in the ultrasonic transmitting member 120 has the recess 133, and the first surface 162 of the probe-side transmitting portion 160 in the probe member 190 is flat. On the contrary, as shown in FIG. 9, this modification example is configured so that the first surface 132 of the transducer-side transmitting portion 130 is flat, and the first surface 162 of the probe-side transmitting portion 160 has a recess 163. The configuration in other respects is similar to that of the above-mentioned embodiment.

In this modification example as well, both of the first surface 132 and the first surface 162 are free ends at a part provided with the recess 163. Therefore, similarly to the above-mentioned embodiment, this configuration also leads to the effect that, even when the frequency characteristics of the ultrasonic transmitting member 120 or the probe member 190 change to some extent, the connection position 150 at the boundary between the ultrasonic transmitting member 120 and the probe member 190 substantially corresponds to an antinode of the vibration.

Second Modification Example

Figure 10:
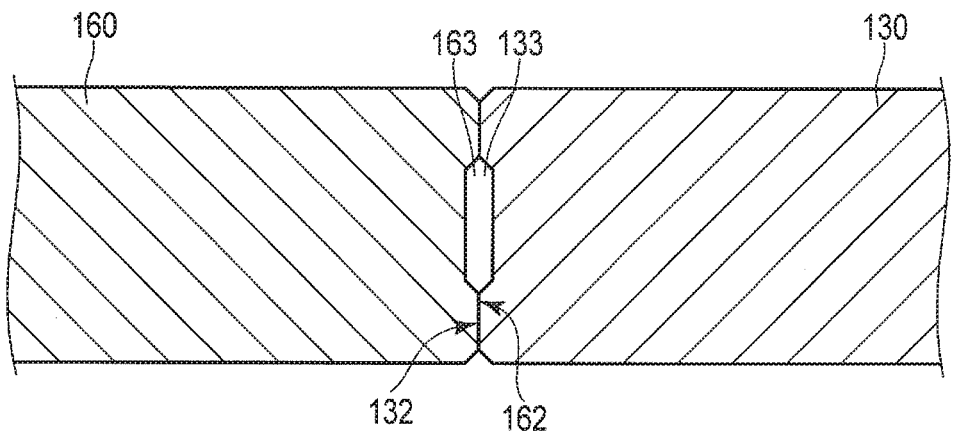
FIG. 10 shows one example of the configuration of the transducer-side transmitting portion and the probe-side transmitting portion in a second modification example.

Referring to FIG. 10, the configuration of a second modification example is described below. In the main embodiment, the first surface 132 of the transducer-side transmitting portion 130 in the ultrasonic transmitting member 120 has the recess 133, and the first surface 162 of the probe-side transmitting portion 160 in the probe member 190 is flat. In this modification example, as illustrated in FIG. 10, this modification example is configured so that the first surface 162 of the probe-side transmitting portion 160 also has a recess 163. The recess 133 at the first surface 132 and the recess 163 at the first surface 162 are disposed at mutually corresponding positions. The configuration in other respects is similar to that of the above-mentioned embodiment.

In this modification example as well, both of the first surface 132 and the first surface 162 are free ends at a part provided with the recess 133 at the first surface 132 and the recess 163 at the first surface 162. Therefore, similarly to the above-mentioned embodiment, this configuration also leads to the effect that, even when the frequency characteristics of the ultrasonic transmitting member 120 or the probe member 190 change to some extent, the connection position 150 at the boundary between the ultrasonic transmitting member 120 and the probe member 190 corresponds to an antinode of the vibration.

Third Modification Example

Figure 11:
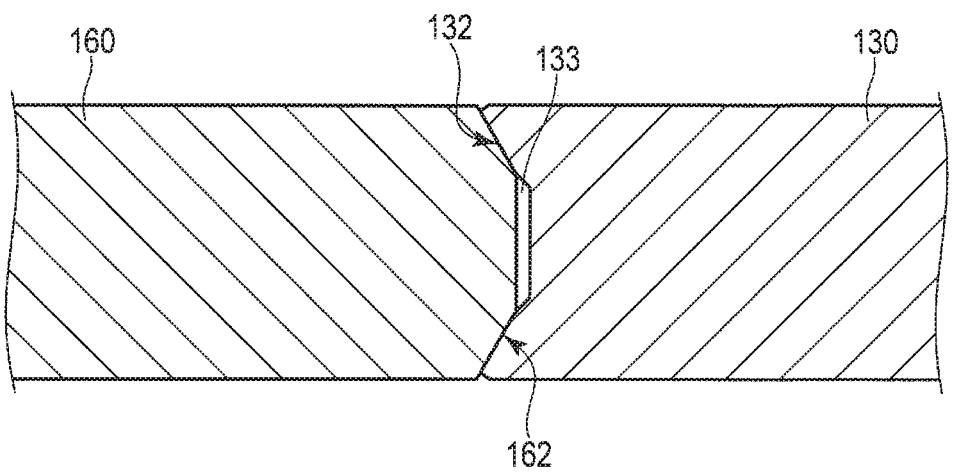
FIG. 11 shows one example of the configuration of the transducer-side transmitting portion and the probe-side transmitting portion in a third modification example.

Referring to FIG. 11, the configuration of a third modification example is described below. In the main embodiment, the contact face 134 where the first surface 132 of the transducer-side transmitting portion 130 and the first surface 162 of the probe-side transmitting portion 160 are in contact is substantially perpendicular to the center axis of the transducer-side transmitting portion 130 and the probe-side transmitting portion 160. In this embodiment, as illustrated in FIG. 11, for example, this modification example is configured so that the first surface 132 of the transducer-side transmitting portion 130 contains a depression towards the longitudinal axis, and the first surface 162 of the probe-side transmitting portion 160 protrudes more toward the longitudinal axis. The configuration in other respects is similar to that of the above-mentioned embodiment. A recess 133 is provided at the first surface, for example, whereby the first surface 132 of the transducer-side transmitting portion 130 and the first surface 162 of the probe-side transmitting portion 160 have one or more contacting portions and one or more non-contacting portions.

In this modification example as well, both of the first surface 132 and the first surface 162 are free ends at a part provided with the recess 133. Therefore, similarly to the above-mentioned embodiment, this configuration also leads to the effect that, even when the frequency characteristics of the ultrasonic transmitting member 120 or the probe member 190 change to some extent, the connection position 150 at the boundary between the ultrasonic transmitting member 120 and the probe member 190 corresponds to an antinode of the vibration.

Note that the first surface 132 of the transducer-side transmitting portion 130 may protrude even more toward the center, and the first surface 162 of the probe-side transmitting portion 160 may become even deeper toward the center. In this case also, a similar effect can be obtained.

Fourth Modification Example

Figure 12:
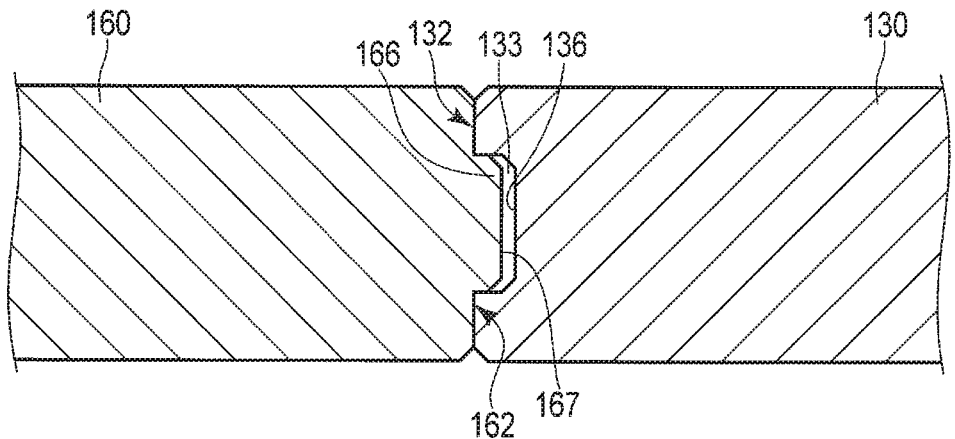
FIG. 12 shows one example of the configuration of the transducer-side transmitting portion and the probe-side transmitting portion in a fourth modification example.

Referring to FIG. 12, the configuration of a fourth modification example is described below. In the main embodiment, the first surface 132 of the transducer-side transmitting portion 130 in the ultrasonic transmitting member 120 has the recess 133, and the first surface 162 of the probe-side transmitting portion 160 in the probe member 190 is flat. In this embodiment, as illustrated in FIG. 12, this modification example is configured so that the first surface 162 of the probe-side transmitting portion 160 has a protrusion 166 at a position corresponding to the recess 133 of the first surface 132. Therefore, the protrusion at the first surface 162 is substantially fitted into the recess 133 at the first surface 132 and probe-side transmitting portion 160 (second member) is press-fit to the transducer-side transmitting portion 130 (first member). Herein, the recess 133 at the first surface 132 has a depth that is larger than the height of the protrusion 166 at the first surface 162. Thus, the bottom part 136 of the recess 133 at the first surface 132 is not in contact with a top 167 of the protrusion 166 at the first surface 162.

In this modification example as well, both of the bottom part 136 of the recess 133 and the top 167 of the protrusion 166 are free ends. Therefore, similarly to the above-mentioned embodiment, this configuration also leads to the effect that, even when the frequency characteristics of the ultrasonic transmitting member 120 or the probe member 190 change to some extent, the connection position 150 at the boundary between the ultrasonic transmitting member 120 and the probe member 190 corresponds to an antinode of the vibration.

Note here that the first surface 132 may have a protrusion, and the first surface 162 may have a recess. In this case also, a similar effect can be obtained.

Fifth Modification Example

Figure 13:
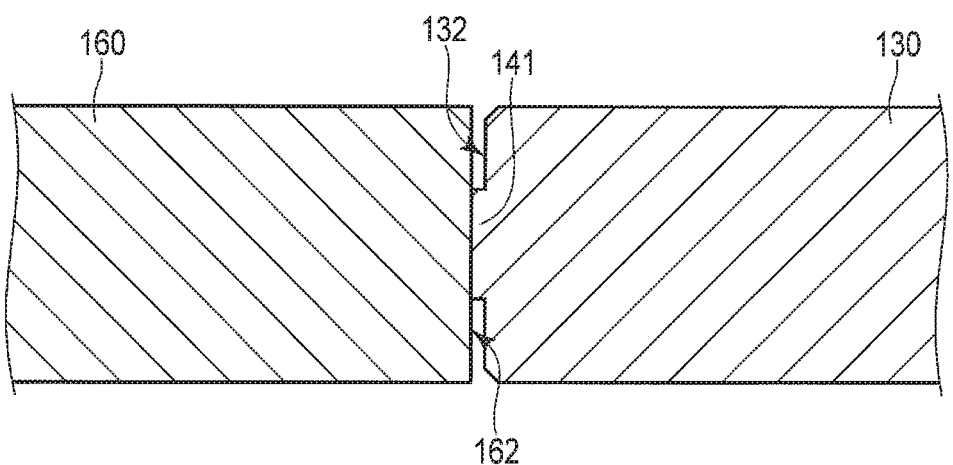
FIG. 13 shows one example of the configuration of the transducer-side transmitting portion and the probe-side transmitting portion in a fifth modification example.

Referring to FIG. 13, the configuration of a fifth modification example is described below. In the main embodiment, the first surface 132 of the transducer-side transmitting portion 130 in the ultrasonic transmitting member 120 has the recess 133, and the first surface 162 of the probe-side transmitting portion 160 in the probe member 190 is flat. In this embodiment, as illustrated in FIG. 13, this modification example is configured so that the first surface 132 of the transducer-side transmitting portion 130 has a protrusion 141 about the longitudinal axis. The first surface 162 of the probe-side transmitting portion 160 is flat. The configuration in other respects is similar to that of the above-mentioned embodiment.

In this modification example as well, although the first surface 132 and the first surface 162 are in contact at a part provided with the protrusion 141, both of the first surface 132 and the first surface 162 are free ends. Therefore, similarly to the above-mentioned embodiment, this configuration also leads to the effect that, even when the frequency characteristics of the ultrasonic transmitting member 120 or the probe member 190 change to some extent, the connection position 150 at the boundary between the ultrasonic transmitting member 120 and the probe member 190 corresponds to an antinode of the vibration. Herein, the contact face between the first surface 132 of the first surface 162 may have any shape. This may be a circle, or a polygon including a rectangle, for example.

Note here that the first surface 132 may be flat, and the first surface 162 may have a protrusion. Alternatively, both of the first surface 132 and the first surface 162 may have a protrusion. In these cases also, a similar effect can be obtained.

Sixth Modification Example

Figure 14:
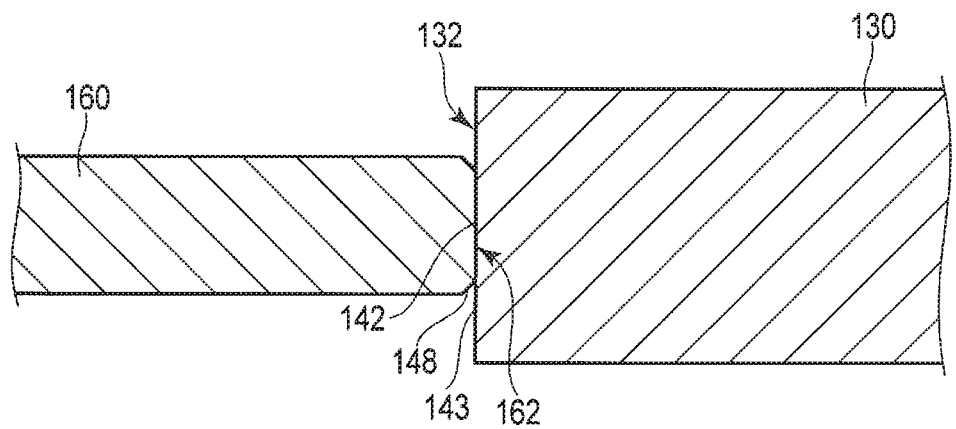
FIG. 14 shows one example of the configuration of the transducer-side transmitting portion and the probe-side transmitting portion in a sixth modification example.

Referring to FIG. 14, the configuration of a sixth modification example is described roughly below. In the main embodiment, the transducer-side transmitting portion 130 of the ultrasonic transmitting member 120 and the probe-side transmitting portion 160 of the probe member 190 have substantially the same thickness. That is, the outline of the boundary face that is visible when the transducer-side transmitting portion 130 is viewed from the probe-side transmitting portion 160 and the outline of the boundary face that is visible when the probe-side transmitting portion 160 is viewed from the transducer-side transmitting portion 130 are substantially the same. In this embodiment, as illustrated in FIG. 14, this modification example is configured so that the transducer-side transmitting portion 130 is thicker than the probe-side transmitting portion 160. Therefore, the first surface 132 of the transducer-side transmitting portion 130 includes a contacting area 142 that is in contact with the first surface 162 of the probe-side transmitting portion 160 and a non-contacting area 143 that is not in contact with the first surface 162. The outer edge of the contact face 162 is chamfered, so that a chamfered part 148 is formed that is inclined with reference to the contact face 162.

In this modification example as well, the first surface 132 is a free end at the non-contacting area 143. Therefore, similarly to the above-mentioned embodiment, this configuration also leads to the effect that, even when the frequency characteristics of the ultrasonic transmitting member 120 or the probe member 190 change to some extent, the connection position 150 at the boundary between the ultrasonic transmitting member 120 and the probe member 190 corresponds to an antinode of the vibration.

Note here that the probe-side transmitting portion 160 may be thicker than the transducer-side transmitting portion 130. In this case also, a similar effect can be obtained.

Seventh Modification Example

Figure 15:
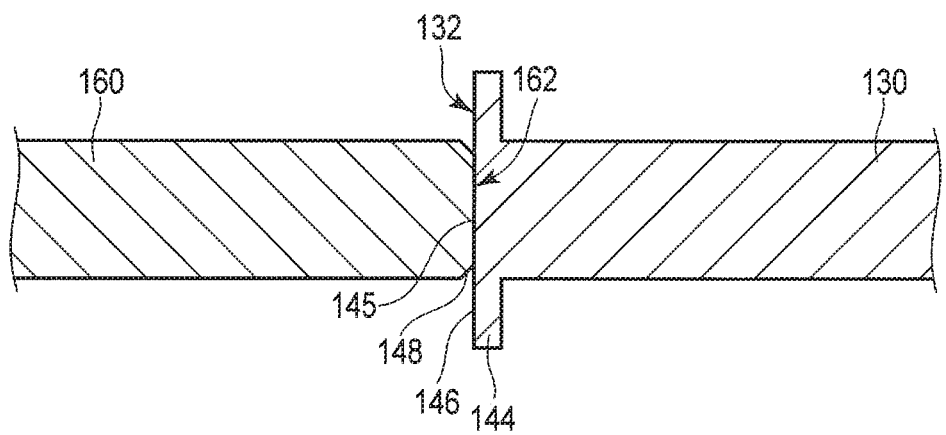
FIG. 15 shows one example of the configuration of the transducer-side transmitting portion and the probe-side transmitting portion in a seventh modification example.

Referring to FIG. 15, the configuration of a seventh modification example is described below. In this modification example, although the transducer-side transmitting portion 130 of the ultrasonic transmitting member 120 and the probe-side transmitting portion 160 of the probe member 190 have substantially the same thickness, a flange 144 is disposed at a distal-end part of the transducer-side transmitting portion 130. Therefore, as illustrated in FIG. 15, the first surface 132 of the transducer-side transmitting portion 130 includes a contacting area 145 that is in contact with the first surface 162 of the probe-side transmitting portion 160 and a non-contacting area 146 that is not in contact with the face.

In this modification example, the first surface 132 is a free end at the non-contacting area 146. The outer edge of the contact face 162 is chamfered, so that the chamfered part 148 is formed that is inclined with reference to the contact face 162. Therefore, similarly to the main embodiment, this configuration also leads to the effect that, even when the frequency characteristics of the ultrasonic transmitting member 120 or the probe member 190 change to some extent, the connection position 150 at the boundary between the ultrasonic transmitting member 120 and the probe member 190 corresponds to an antinode of the vibration.

Note here that a flange may be disposed at the probe-side transmitting portion 160. In this case also, a similar effect can be obtained.

In the above-mentioned embodiment, the ultrasonic transmitting member 120 and the probe member 190 are pushed against each other by the elastic force of the coil spring 68. This is not a limited example as long as ultrasonic transmitting member 120 and the probe member 190 are not screwed together. The ultrasonic transmitting member 120 and the probe member 190 may be pushed against each other by an elastic force of another elastic body. Alternatively, the ultrasonic transmitting member 120 and the probe member 190 may be pushed against each other by another force, such as a magnetic force. This can apply to any of the modification examples.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. An ultrasonic treatment device, comprising:
   an ultrasonic transmitting member configured to extend along a longitudinal axis, the ultrasonic transmitting member configured to transmit a vibration along the longitudinal axis; and
   a probe member configured to extend along the longitudinal axis, the probe member being connected to the ultrasonic transmitting member, the probe member configured to transmit the vibration along the longitudinal axis and contact the ultrasonic transmitting member, wherein at a boundary between the ultrasonic transmitting member and the probe member, the ultrasonic transmitting member comprising a boundary surface, the boundary surface comprising a first contacting area and a first non-contacting area, wherein the first contacting area comprises a perpendicular surface that is perpendicular to the longitudinal axis, wherein:

the first contacting area is in contact with the probe member, and the first non-contacting area is not in contact with the probe member, wherein the first non-contacting area is a free end and corresponds to an antinode position, and wherein the first non-contacting area does not protrude toward the probe member relative to the perpendicular surface of the ultrasonic transmitting member, wherein the probe member comprises a second boundary surface, the second boundary surface comprises a second contacting area and a second non-contacting area, wherein the second contacting area comprises a second perpendicular surface that is perpendicular to the longitudinal axis, wherein:

the second contacting area is in contact with the ultrasonic transmitting member, the second non-contacting area is not in contact with the ultrasonic transmitting member, and does not protrude toward the ultrasonic transmitting member relative to the second perpendicular surface, and the second perpendicular surface is in contact with the perpendicular surface of the ultrasonic transmitting member, and wherein the perpendicular surface of the ultrasonic transmitting member and the second perpendicular surface of the probe member are configured to correspond to an antinode position of the vibration.

2. The ultrasonic treatment device according to claim 1, wherein the first contacting area has an annular shape.

3. The ultrasonic treatment device according to claim 2, wherein the first contacting area of the ultrasonic transmitting member protrudes further toward the probe member than the first non-contacting area.

4. The ultrasonic treatment device according to claim 3, wherein at the boundary, the probe member comprises the second boundary surface comprising the second contacting area that is in contact with the ultrasonic transmitting member, and the second non-contacting area that is not in contact with the ultrasonic transmitting member, and the second contacting area of the probe member protrudes further toward the ultrasonic transmitting member than the second non-contacting area.

5. The ultrasonic treatment device according to claim 3, wherein at the boundary, the probe member comprises the second boundary surface comprising the second contacting area that is in contact with the ultrasonic transmitting member, and the second non-contacting area that is not in contact with the ultrasonic transmitting member, and the second non-contacting area of the probe member protrudes further toward the ultrasonic transmitting member than the second contacting area.

6. The ultrasonic treatment device according to claim 3, wherein at the boundary, the probe member comprises the second boundary surface comprising the second contacting area that is in contact with the ultrasonic transmitting member, and the second non-contacting area that is not in contact with the ultrasonic transmitting member, wherein the second non-contacting area is a chamfered surface that is inclined with reference to the second contacting area.

7. The ultrasonic treatment device according to claim 1, wherein the first non-contacting area comprises a surface that is perpendicular to the longitudinal axis.

8. The ultrasonic treatment device according to claim 7, wherein the first contacting area comprises a surface that is perpendicular to the longitudinal axis, and at the boundary, the first non-contacting area is disposed along an outer edge of the first contacting area.

9. The ultrasonic treatment device according to claim 1, wherein at the boundary, the boundary surface of the ultrasonic transmitting member and the second boundary surface of the probe member have a same shape.

10. The ultrasonic treatment device according to claim 1, wherein the ultrasonic transmitting member is configured to connect with the probe member by being pushed against each other.

11. The ultrasonic treatment device according to claim 1, wherein the probe member is press-fit to the ultrasonic transmitting member.

* * * * *